United States Patent [19]

Kleiner

[11] Patent Number: 4,839,105

[45] Date of Patent: Jun. 13, 1989

[54] PROCESS FOR THE PREPARATION OF ALKANEPHOSPHONOUS ACIDS

[75] Inventor: Hans-Jerg Kleiner, Kronberg, Fed. Rep. of Germany

[73] Assignee: Hoechst Aktiengesellschaft, Frankfurt am Main, Fed. Rep. of Germany

[21] Appl. No.: 217,132

[22] Filed: Jun. 29, 1988

Related U.S. Application Data

[63] Continuation of Ser. No. 91,318, Aug. 28, 1987, abandoned, which is a continuation of Ser. No. 692,836, Jan. 18, 1985, abandoned.

[30] Foreign Application Priority Data

Jan. 21, 1984 [DE] Fed. Rep. of Germany ....... 3402018

[51] Int. Cl.$^4$ ................................................ C07F 9/48
[52] U.S. Cl. ............................................ 260/502.4 R
[58] Field of Search ................................. 260/502.4 R

[56] References Cited

U.S. PATENT DOCUMENTS

| | | | |
|---|---|---|---|
| 2,584,112 | 2/1952 | Brown | 260/502.4 R |
| 3,833,662 | 9/1974 | Staendeke et al. | 260/502.4 R |
| 4,485,052 | 11/1984 | Kleiner et al. | 260/502.4 R |

OTHER PUBLICATIONS

Frank, "The Phosphonous Acids and Their Derivatives", Chem. Rev. vol. 61, No. 4, Aug. 1961, p. 394.
Van Wazer, "Phosphorus and its Compounds" vol. 1, Chemistry, 1958, p. 353.
Berlin et al, "Chem. Reviews", 60(1960) Jun, pp. 243–260, 243, 255, 259 and 260.
Houben-Weyl, vol. XII/1, pp. 69 and 225 (1963).
Houben-Weyl, vol. E1, p. 240 (1982).

*Primary Examiner*—J. E. Evans
*Attorney, Agent, or Firm*—Curtis, Morris & Safford

[57] ABSTRACT

Preparation of alkanephosphonous acids of the formula

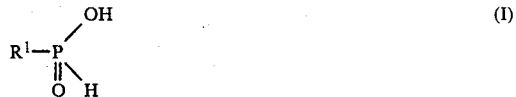

in which R1 denotes alkyl, by reacting monoalkylphosphanes of the formula

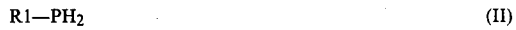

with H2O2 in a solution containing hydrochloric acid.

4 Claims, No Drawings

PROCESS FOR THE PREPARATION OF ALKANEPHOSPHONOUS ACIDS

This application is a continuation of application Ser. No. 091,318, filed Aug. 28, 1987, now abandoned, which in turn is a continuation of application Ser. No. 692,836, filed Jan. 18, 1985, now abandoned.

Alkanephosphonous acids are useful intermediates for the preparation of plant protection agents and flame-proofing agent. Various salts of short-chain alkanephosphonous acids have been proposed as fungicidal agents (European Pat. No. 0,038,778).

Alkanephosphonous acids are prepared, for example, by hydrolysis of alkyl-dichloro-phosphanes (German Offenlegungsschrift 3,146,196). They are also formed when monoalkylphosphanes are oxidized. The latter are formed, inter alia, as by-products—in some cases in small amounts—in industrial processes (c.f. German Auslegeschrift 2,540,283; European Published Specification 0,026,278). Because they are easily oxidized, are extremely toxic and have a repugnant odor, they must be rendered harmless by further processing. Conversion of monoalkylphosphanes obtained as by-products into useful, acceptable secondary products is therefore additionally of importance.

It is already known that monoalkylphosphanes can be oxidized to alkanephosphonous acids with hydrogen peroxide (Houben-Weyl, Volume XII/1, page 297; U.S. Pat. No. 2,584,112). Acetic acid is proposed as an advantageous solvent in U.S. Pat. No. 2,584,112, and molybdenum oxide is proposed as the activator. However, relatively large amounts of phosphoric acid and alkanephosphonic acids are formed as by-products in this process. For example, 10% of phosphoric acid and 13% of phosphonic acid are obtained in the oxidation of tert.-dodecylphosphane at 50° C.

It has now been found, surprisingly, that pure alkanephosphonous acids of the general formula I

in which R1 denotes $(C_1-C_{12})$-alkyl groups, preferably the methyl or ethyl group, can be prepared by reacting monoalkylphosphanes of the general formula II

with essentially stoichiometric amounts of hydrogen peroxide in a solution containing hydrochloric acid.

Examples of suitable monoalkylphosphanes are methyl-, ethyl-, butyl- and octyl-phosphane.

The phosphanes are dissolved in hydrochloric acid, the concentration of which should not be below about 5%. The lower limit of the concentration of the phosphanes in the hydrochloric acid can be as little as 0.0001% by weight. Because of the low basicity of the phosphanes and the volatility, in particular of the lower homologs, care should be taken that the hydrogen chloride is always present in a significant stoichiometric excess. If necessary, hydrogen chloride can be metered in during the addition of the hydrogen peroxide, in order to guarantee a sufficiently high concentration of H+ ions in the reaction mixture.

Hydrogen peroxide is advantageously added in concentrated aqueous solution, for example 30 or 35% strength. If stoichiometric amounts are used, 2 moles of hydrogen peroxide are required for the oxidation of 1 mole of phosphane. If low temperatures are maintained, it is also possible to employ a slight excess of H2O2 without further oxidation to the alkanephosphonic acids occurring.

It may be advantageous to carry out the reaction under an inert gas atmosphere (nitrogen).

The reaction is carried out between 0° and the boiling point of the mixture, preferably at 20° to 100° C. The reaction is exothermic. If necessary, the reaction temperature must be maintained by cooling. If desired, the reaction can also be carried out under pressure.

The reaction solutions are worked up in a simple manner by distilling off the water and the hydrogen chloride. In the isolation of methane- and ethanephosphonous acid, internal temperatures of 90°-100° C. should not be exceeded, since the phosphonous acids otherwise partly decompose. Residual contents of hydrogen chloride in the end products can be largely removed at 80°-100° C. by applying a vacuum or by stripping with nitrogen.

The process of the present Application is of particular interest for the treatment of phosphane-containing waste hydrochloric acids such as are obtained in industrial processes. It gives alkanephosphonous acids in a purity of over 95%. Even in the presence of large amounts of alkanephosphonous acids, virtually no further oxidation to alkanephosphonic acids or phosphoric acid occurs before the oxidation of the monoalkylphosphanes to the alkanephosphonous acids has ended. It is particularly surprising that this also applies to the first members of the homologous monoalkylphosphanes, i.e. methyl- and ethyl-phosphane, since it is known that as the chain length decreases, the monoalkylphosphanes become more unstable towards oxidizing agents. Conversion into the phosphonic acids was therefore to be expected (Houben-Weyl, Volume XII/1, pages 69 and 359).

EXAMPLE 1

21.8 g of 35% strength (0.225 mole) hydrogen peroxide solution are added dropwise to 250 g of concentrated hydrochloric acid containing 5.4 g (0.13 mole) of methylphosphane in the course of 45 minutes, with cooling and stirring and while flushing with nitrogen. When the reaction has ended, it can be seen from the 31P-NMR spectrum that the solution formed of methanephosphonous acid in hydrochloric acid contains only about 2% of methanephosphonic acid, based on the total phosphorus.

EXAMPLE 2

4.5 g of 35% strength (0.047 mole) hydrogen peroxide solution are added dropwise to 1 kg of 16% strength hydrochloric acid containing 1.1 g (0.023 mole) of methylphosphane at 30° C., with stirring and under a nitrogen atmosphere and with gentle warming. The solution is then carefully concentrated in vacuo at 30°-40° C. The resulting solution of methanephosphonous acid shows no impurities in the 31P-NMR spectrum.

EXAMPLE 3

32.4 g of 35% strength (0.334 mole) hydrogen peroxide solution are added dropwise to 223 g of concentrated hydrochloric acid containing 8 g (0.166 mole) of methylphosphane at 85° C., with gentle cooling, with stirring and under a nitrogen atmosphere. After 40 minutes, the reaction has ended. It can be seen from the 31P-NMR spectrum that the solution formed of methanephosphonous acid in hydrochloric acid contains 2.7% of methanephosphonic acid, 0.5% of phosphorous acid and 0.6% of phosphoric acid, based on the total phosphorus.

I claim:

1. A process for the preparation of an alkanephosphonous acid of the formula

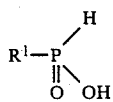

in which $R^1$ denotes $(C_1-C_{12})$-alkyl, which comprises reacting a monoalkylphosphane of the formula $$R^1-PH_2 \qquad (II)$$

with an essentially stoichiometric amount of hydrogen peroxide in concentrated hydrochloric acid at a temperature between 0° C. and the boiling point of the mixture, such that the alkanephosphonous acid is formed in the hydrochloric acid solution in a purity of over 95%.

2. The process as claimed in claim 1, wherein the reaction is carried out at 20°–100° C.

3. The process as claimed in claim 1, wherein the reaction is carried out in a nitrogen atmosphere.

4. The process as claimed in claim 1, wherein the reaction is carried out under pressure.

* * * * *